(12) United States Patent
Peeters et al.

(10) Patent No.: US 8,909,391 B1
(45) Date of Patent: Dec. 9, 2014

(54) RESPONSIVE NAVIGATION OF AN UNMANNED AERIAL VEHICLE TO A REMEDIAL FACILITY

(71) Applicant: Google Inc., Mountain View, CA (US)

(72) Inventors: Eric Peeters, Mountain View, CA (US); Eric Teller, Palo Alto, CA (US); William Graham Patrick, San Francisco, CA (US)

(73) Assignee: Google Inc., Mountain View, CA (US)

( * ) Notice: Subject to any disclaimer, the term of this patent is extended or adjusted under 35 U.S.C. 154(b) by 60 days.

(21) Appl. No.: 13/730,110

(22) Filed: Dec. 28, 2012

(51) Int. Cl.
G06Q 10/00 (2012.01)
G05D 1/00 (2006.01)

(52) U.S. Cl.
CPC .................................. G05D 1/0011 (2013.01)
USPC .............................................. 701/2; 709/201

(58) Field of Classification Search
USPC .............................................. 701/2; 709/201
See application file for complete search history.

(56) References Cited

U.S. PATENT DOCUMENTS

| | | | |
|---|---|---|---|
| 6,056,237 A | 5/2000 | Woodland | |
| 6,567,044 B2 | 5/2003 | Carroll | |
| 6,817,573 B2 | 11/2004 | Harrison et al. | |
| 6,965,816 B2 | 11/2005 | Walker | |
| 7,574,193 B2 | 8/2009 | Hulkkonen et al. | |
| 7,813,888 B2 | 10/2010 | Vian et al. | |
| 7,877,785 B2 | 1/2011 | Selignan | |
| 8,028,952 B2 | 10/2011 | Urnes, Sr. | |
| 2007/0049251 A1 | 3/2007 | Mock et al. | |
| 2008/0085732 A1 | 4/2008 | Mizuide et al. | |
| 2010/0084513 A1 | 4/2010 | Gariepy et al. | |
| 2010/0256839 A1 | 10/2010 | Fitzpatrick | |
| 2010/0280699 A1 | 11/2010 | Bageshwar et al. | |
| 2011/0084162 A1 | 4/2011 | Goossen et al. | |
| 2011/0128372 A1 | 6/2011 | Malecki et al. | |
| 2011/0130636 A1* | 6/2011 | Daniel et al. ................... 600/301 |
| 2011/0267241 A1 | 11/2011 | Grimm et al. | |
| 2011/0281679 A1 | 11/2011 | Larrabee et al. | |
| 2011/0315806 A1 | 12/2011 | Piasecki et al. | |
| 2012/0080556 A1 | 4/2012 | Root, Jr. | |
| 2012/0152654 A1 | 6/2012 | Marcus | |

OTHER PUBLICATIONS

Mitchell J.H. Lum, et al., Telesurgery Via Unmanned Aerial Vehicle (UAV) with a Field Deployable Surgical Robot, Medicine Meets Virtual Reality 15, Feb. 2007, Long Beach, California.

H.S. Nguyen, et al., Situation Identification by Unmanned Aerial Vehicle, Institute of Mathematics, 2001, pp. 49-56, Warsaw University.

Elizabeth Bone et al., Unmanned Aerial Vehicles: Background and Issues for Congress, Report for Congress, Congressional Research Service, The Library of Congress, Apr. 25, 2003.

* cited by examiner

*Primary Examiner* — Mary Cheung
*Assistant Examiner* — Yuen Wong
(74) *Attorney, Agent, or Firm* — McDonnell Boehnen Hulbert & Berghoff LLP

(57) ABSTRACT

The present disclosure relates to a deployment system for an unmanned aerial vehicle (UAV). In one aspect, an illustrative deployment system includes a communication system configured for receiving diagnostic data corresponding to an object held by a UAV, wherein the object has an expiration condition; and a logic module configured for (i) determining that the expiration condition has been satisfied based, at least in part, on the received diagnostic data, and (ii) responsive to determining that the expiration condition has been satisfied, initiating an action that includes sending to the UAV both (a) navigation data relating to a remedial facility, and (b) instructions to navigate to the remedial facility based, at least in part, on the navigation data.

25 Claims, 9 Drawing Sheets

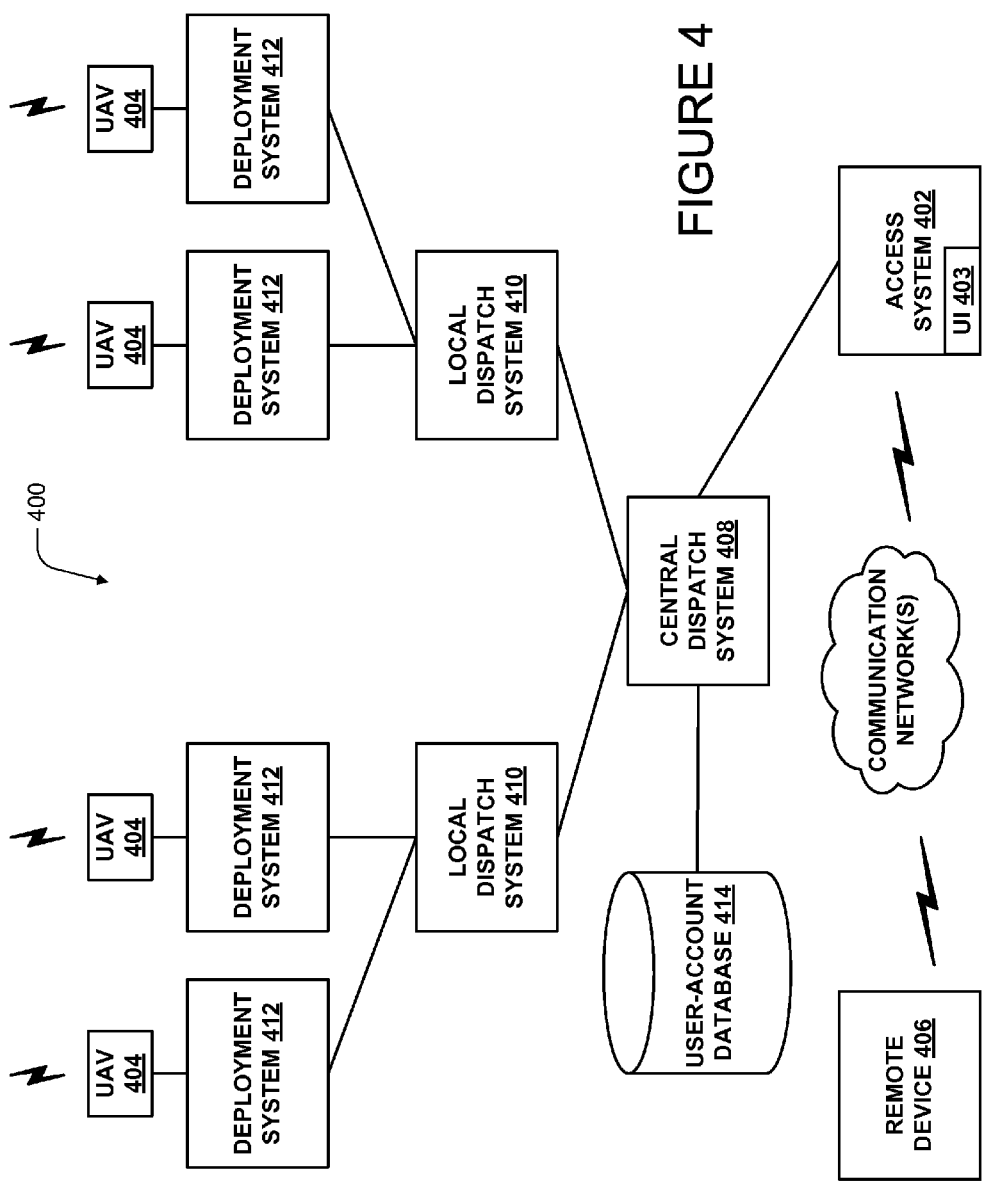

RESPONSIVE NAVIGATION OF AN UNMANNED AERIAL VEHICLE TO A REMEDIAL FACILITY

BACKGROUND

Unless otherwise indicated herein, the materials described in this section are not prior art to the claims in this application and are not admitted to be prior art by inclusion in this section.

An unmanned vehicle, which may also be referred to as an autonomous vehicle, is a vehicle capable of travel without a physically-present human operator. An unmanned vehicle may operate in a remote-control mode, in an autonomous mode, or in a partially autonomous mode.

When an unmanned vehicle operates in a remote-control mode, a pilot or driver that is at a remote location can control the unmanned vehicle via commands that are sent to the unmanned vehicle via a wireless link. When the unmanned vehicle operates in autonomous mode, the unmanned vehicle typically moves based on pre-programmed navigation way-points, dynamic automation systems, or a combination of these. Further, some unmanned vehicles can operate in both a remote-control mode and an autonomous mode, and in some instances may do so simultaneously. For instance, a remote pilot or driver may wish to leave navigation to an autonomous system while manually performing another task, such as operating a mechanical system for picking up objects, as an example.

Various types of unmanned vehicles exist for various different environments. For instance, unmanned vehicles exist for operation in the air, on the ground, underwater, and in space. Unmanned vehicles also exist for hybrid operations in which multi-environment operation is possible. Examples of hybrid unmanned vehicles include an amphibious craft that is capable of operation on land as well as on water or a floatplane that is capable of landing on water as well as on land. Other examples are also possible.

BRIEF SUMMARY

In one aspect, an illustrative deployment system includes a communication system configured for receiving diagnostic data corresponding to an object included in an unmanned aerial vehicle (UAV), wherein the object has an expiration condition; and a logic module configured for (i) determining that the expiration condition has been satisfied based, at least in part, on the received diagnostic data, and (ii) responsive to determining that the expiration condition has been satisfied, initiating an action that includes sending to the UAV both (a) navigation data relating to a remedial facility, and (b) instructions to navigate to the remedial facility based, at least in part, on the navigation data.

In another aspect, an illustrative method involves: receiving, by a deployment system, diagnostic data corresponding to an object included in a UAV, wherein the object has an expiration condition; determining that the expiration condition has been satisfied based, at least in part, on the received diagnostic data; and responsive to determining that the expiration condition has been satisfied, initiating an action that includes sending to the UAV both (i) navigation data relating to a remedial facility, and (ii) instructions to navigate to the remedial facility based, at least in part, on the navigation data.

In another aspect, an illustrative computer-readable storage has stored thereon program instructions that, when executed by a processor, cause performance of a set of functions, the set including: receiving, by a deployment system, diagnostic data corresponding to an object included in a UAV, wherein the object has an expiration condition; determining that the expiration condition has been satisfied based, at least in part, on the received diagnostic data; and responsive to determining that the expiration condition has been satisfied, initiating an action that includes sending to the UAV both (i) navigation data relating to an remedial facility, and (ii) instructions to navigate to the remedial facility based, at least in part, on the navigation data.

In another aspect, an illustrative deployment system an item having an expiration condition; and a logic module configured for (i) determining diagnostic data corresponding to the item, (ii) determining that the expiration condition has been satisfied based, at least in part, on the determined diagnostic data, and (ii) responsive to determining that the expiration condition has been satisfied, initiating an action that includes sending to a UAV (a) navigation data relating to a remedial facility, and (b) instructions to retrieve the item and navigate with the retrieved item to the remedial facility based, at least in part, on the navigation data.

In another aspect, an illustrative UAV includes a navigation module; an object having an expiration condition; and a logic module configured for: (i) determining diagnostic data corresponding to the object; (ii) determining that the expiration condition has been satisfied based, at least in part, on the determined diagnostic data; and (iii) responsive to determining that the expiration condition has been satisfied, initiating an action that includes the UAV using the navigation module to navigate to a remedial facility.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 4 is a simplified block diagram illustrating a medical support system, according to an example embodiment.

DETAILED DESCRIPTION

Figure 1:
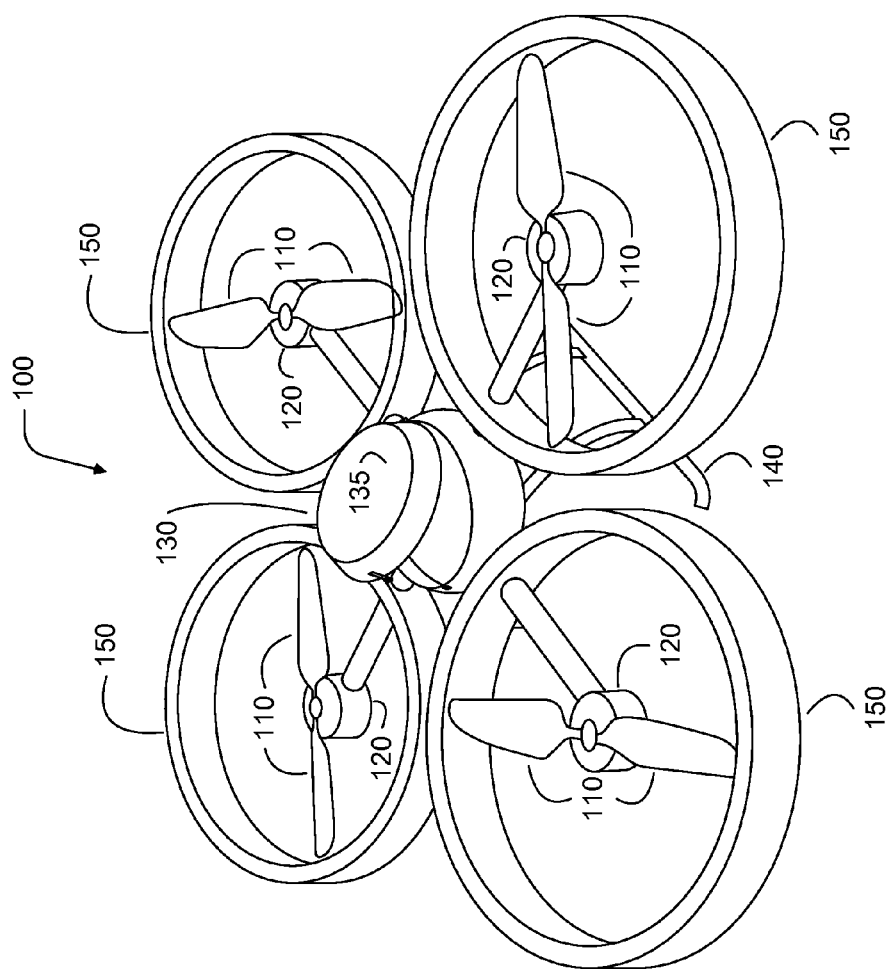
FIGS. 1, 2, 3A, and 3B are simplified illustrations of unmanned aerial vehicles, according to example embodiments.

Throughout this disclosure, the term "a" or "an" refers to "at least one," and the term "the" refers to "the at least one," unless otherwise specified.

Exemplary systems and methods are described herein. It should be understood that the word "exemplary" is used herein to mean "serving as an example, instance, or illustration." Any embodiment or feature described herein as "exemplary" or "illustrative" is not necessarily to be construed as preferred or advantageous over other embodiments or features. More generally, the embodiments described herein are not meant to be limiting. It will be readily understood that certain aspects of the disclosed systems and methods can be arranged and combined in a wide variety of different configurations, all of which are contemplated herein.

I. Overview

Embodiments described herein may relate to and/or may be implemented in a system in which unmanned vehicles, and in particular, "unmanned aerial vehicles" (UAVs), are configured to provide medical support.

In an illustrative embodiment, a medical-support system may include a fleet of UAVs that are distributed throughout a geographic area, such as a city. The medical-support system may be configured for communications with remote devices, such as mobile phones, so that medical support can be requested by a person in need of such medical support (or by others on behalf of a person in need). The medical-support system can then dispatch the appropriate UAV or UAVs to the scene of the medical situation in order to provide medical support.

In particular, a medical-support system may include a fleet with a number of different types of UAVs, which are configured for different medical situations. For instance, some UAVs may be configured with items and/or functionality that are expected to be helpful in a cardiac-arrest situation, some UAVs may be configured to help a choking victim, some UAVs may be configured to help a trauma victim, and so on. As such, an illustrative medical-support system may be configured to identify or classify the particular type of medical situation that is occurring, to select the appropriate UAV from those that are available, and to dispatch the selected UAV to the scene of the medical situation.

In one illustrative medical-support system, a UAV may be configured to deliver a medical item (e.g., medicine) to a person in need of medical attention. The medical-support system may also include a deployment system for launching the UAV into flight, and/or for providing other functions, such as diagnostic-related functions in connection with a UAV.

Since medicine and other types of medical items may expire (e.g., after an expiration time has lapsed), the deployment system may be configured to handle such instances where a medical item has expired. For example, the deployment system may determine that medicine included in a UAV has expired, and in response, the deployment system may cause the UAV to navigate to a remedial facility where the expired medicine may be easily replaced with current (non-expired) medicine. As such, the UAV may then be used to provide medical attention as needed.

In another illustrative medical-support system, medical items may be stored in the deployment system. In response to the deployment system determining that a medical item has expired, the deployment system may cause a UAV to retrieve the expired item and navigate with the retrieved item to a remedial facility where the item may be replaced. The replacement item may then be returned to the deployment system.

In another illustrative medical-support system, a UAV may itself be configured to perform select diagnostic-related functions in connection with an included object having an expiration condition. As such, the UAV may determine that an expiration condition has been satisfied, and as a result, the UAV may navigate to a remedial facility where the object may be replaced.

Herein, a "medical situation" should be understood to include any situation to which government or private entity, such as a police department, a fire department, and/or an emergency medical services (EMS) entity, might dispatch its personnel. Therefore, some medical situations may in fact be non-medical in nature. For example, an emergency situation to which a police car, fire truck, or ambulance might be dispatched may be considered a medical situation for purposes of this disclosure. Medical support may not be required at such emergency situations (e.g., when police are sent to the scene of a non-violent crime). Further, some non-emergency situations to which a police car, fire truck, ambulance, or the like might be dispatched, may also be considered a medical situation for purposes of this disclosure. Thus, while exemplary embodiments may be described as being implemented to help provide medical support at the scene of a medical situation, those skilled in the art will understand that the UAVs, the functionality of such UAVs, and/or other aspects of the embodiments that are explicitly described herein can also apply in non-medical and/or non-emergency applications.

It should be understood that the above embodiments, and other embodiments described herein, are provided for explanatory purposes, and are not intended to be limiting.

II. Illustrative Unmanned Vehicles

The term "unmanned aerial vehicle," as used in this disclosure, refers to any autonomous or semi-autonomous vehicle that is capable of performing some functions without a physically-present human pilot. Examples of flight-related functions may include, but are not limited to, sensing its environment or operating in the air without a need for input from an operator, among others.

A UAV may be autonomous or semi-autonomous. For instance, some functions could be controlled by a remote human operator, while other functions are carried out autonomously. Further, a UAV may be configured to allow a remote operator to take over functions that can otherwise be controlled autonomously by the UAV. Yet further, a given type of function may be controlled remotely at one level of abstraction and performed autonomously at another level of abstraction. For example, a remote operator could control high level navigation decisions for a UAV, such as by specifying that the UAV should travel from one location to another (e.g., from the city hall in Palo Alto to the city hall in San Francisco), while the UAV's navigation system autonomously controls more fine-grained navigation decisions, such as the specific route to take between the two locations, specific flight controls to achieve the route and avoid obstacles while navigating the route, and so on. Other examples are also possible.

A UAV can be of various forms. For example, a UAV may take the form of a rotorcraft such as a helicopter or multicopter, a fixed-wing aircraft, a jet aircraft, a ducted fan aircraft, a lighter-than-air dirigible such as a blimp or steerable balloon, a tail-sitter aircraft, a glider aircraft, and/or an ornithopter, among other possibilities. Further, the terms "drone", "unmanned aerial vehicle system" ("UAVS"), or "unmanned aerial system" ("UAS") may also be used to refer to a UAV.

FIG. 1 is a simplified illustration of a UAV, according to an example embodiment. In particular, FIG. 1 shows an example of a rotorcraft 100 that is commonly referred to as a multicopter. Multicopter 100 may also be referred to as a quadcopter, as it includes four rotors 110. It should be understood that example embodiments may involve rotorcraft with more or less rotors than multicopter 100. For example, a helicopter typically has two rotors. Other examples with three or more rotors are possible as well. Herein, the term "multicopter" refers to any rotorcraft having more than two rotors, and the term "helicopter" refers to rotorcraft having two rotors.

Referring to multicopter 100 in greater detail, the four rotors 110 provide propulsion and maneuverability for the multicopter 100. More specifically, each rotor 110 includes blades that are attached to a motor 120. Configured as such the rotors may allow the multicopter 100 to take off and land vertically, to maneuver in any direction, and/or to hover. Furthermore, the pitch of the blades may be adjusted as a group and/or differentially, and may allow a multicopter 110 to perform three-dimensional aerial maneuvers such as an upside-down hover, a continuous tail-down "tic-toc," loops, loops with pirouettes, stall-turns with pirouette, knife-edge, immelmann, slapper, and traveling flips, among others. When the pitch of all blades is adjusted to perform such aerial maneuvering, this may be referred to as adjusting the "collective pitch" of the multicopter 100. Blade-pitch adjustment may be particularly useful for rotorcraft with substantial inertia in the rotors and/or drive train, but is not limited to such rotorcraft Additionally or alternatively, multicopter 100 may propel and maneuver itself adjust the rotation rate of the motors, collectively or differentially. This technique may be particularly useful for small electric rotorcraft with low inertia in the motors and/or rotor system, but is not limited to such rotorcraft.

Multicopter 100 also includes a central enclosure 130 with a hinged lid 135. The central enclosure may contain, e.g., control electronics such as an inertial measurement unit (IMU) and/or an electronic speed controller, batteries, other sensors, and/or a payload, among other possibilities.

The illustrative multicopter 100 also includes landing gear 140 to assist with controlled take-offs and landings. In other embodiments, multicopters and other types of UAVs without landing gear are also possible.

In a further aspect, multicopter 100 includes rotor protectors 150. Such rotor protectors 150 can serve multiple purposes, such as protecting the rotors 110 from damage if the multicopter 100 strays too close to an object, protecting the multicopter 100 structure from damage, and protecting nearby objects from being damaged by the rotors 110. It should be understood that in other embodiments, multicopters and other types of UAVs without rotor protectors are also possible. Further, rotor protectors of different shapes, sizes, and function are possible, without departing from the scope of the invention.

A multicopter 100 may control the direction and/or speed of its movement by controlling its pitch, roll, yaw, and/or altitude. To do so, multicopter 100 may increase or decrease the speeds at which the rotors 110 spin. For example, by maintaining a constant speed of three rotors 110 and decreasing the speed of a fourth rotor, the multicopter 100 can roll right, roll left, pitch forward, or pitch backward, depending upon which motor has its speed decreased. Specifically, the multicopter may roll in the direction of the motor with the decreased speed. As another example, increasing or decreasing the speed of all rotors 110 simultaneously can result in the multicopter 100 increasing or decreasing its altitude, respectively. As yet another example, increasing or decreasing the speed of rotors 110 that are turning in the same direction can result in the multicopter 100 performing a yaw-left or yaw-right movement. These are but a few examples of the different types of movement that can be accomplished by independently or collectively adjusting the RPM and/or the direction that rotors 110 are spinning.

As noted above, some embodiments may involve other types of UAVs, in addition or in the alternative to multicopters. For instance, FIGS. 2 and 3 are simplified illustrations of other types of UAVs, according to example embodiments.

Figure 2:
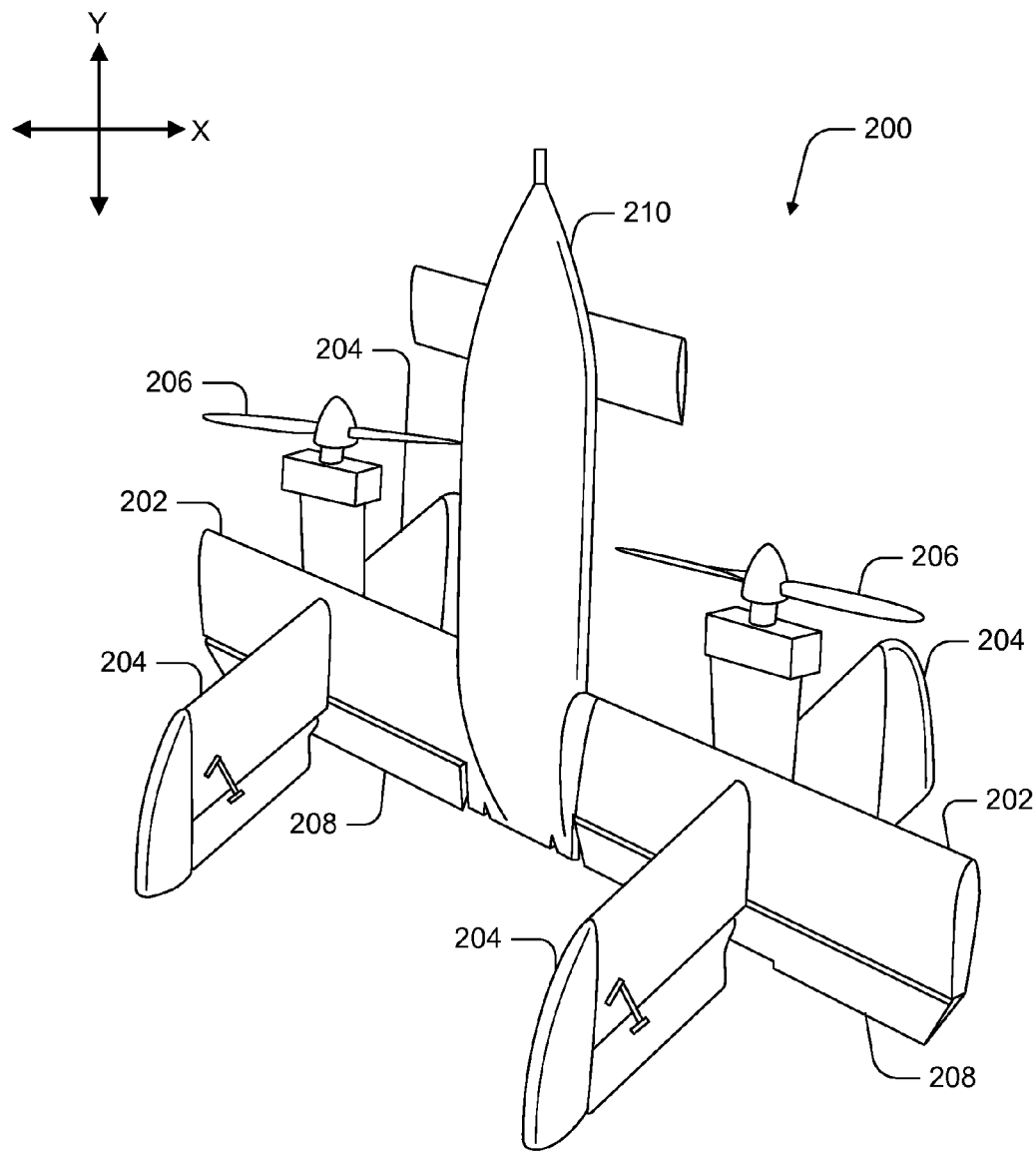

In particular, FIG. 2 shows an example of a fixed-wing aircraft 200, which may also be referred to as an airplane, an aeroplane, or simply a plane. A fixed-wing aircraft 200, as the name implies, has stationary wings 210 that generate lift based on the wing shape and the vehicle's forward airspeed. This wing configuration is different from a rotorcraft's configuration, which produces lift through rotating rotors about a fixed mast, and an ornithopter's configuration, which produces lift by flapping wings.

FIG. 2 depicts some common structures used in a fixed-wing aircraft 200. In particular, fixed-wing aircraft 200 includes a fuselage 220, two horizontal wings 210 with an airfoil-shaped cross section to produce an aerodynamic force, a vertical stabilizer 230 (or fin) to stabilize the plane's yaw (turn left or right), a horizontal stabilizer 240 (also referred to as an elevator or tailplane) to stabilize pitch (tilt up or down), landing gear 250, and a propulsion unit 260, which can include a motor, shaft, and propeller.

Figure 3A:
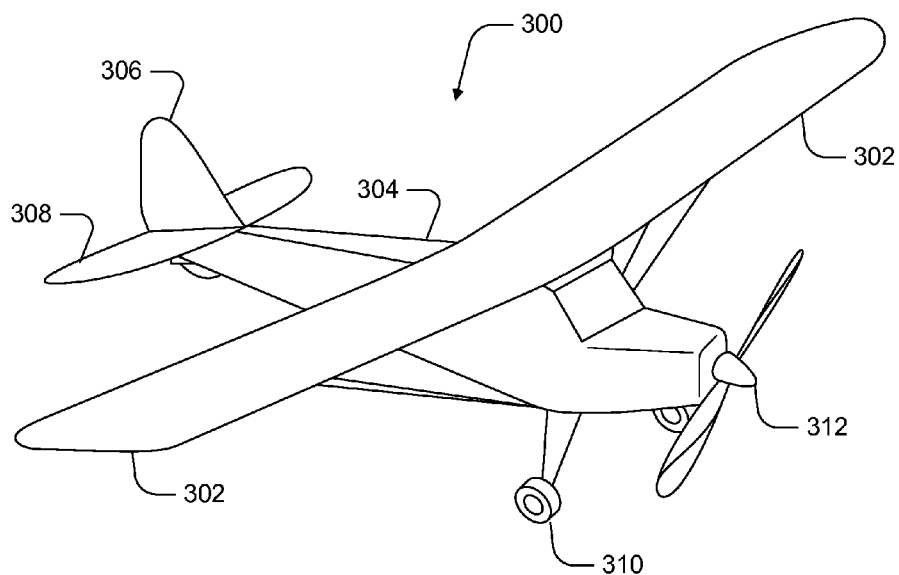
Figure 3B:
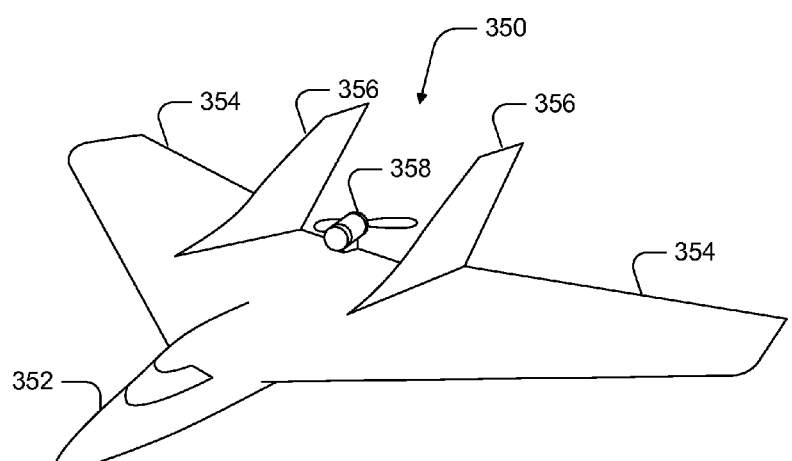

FIG. 3 shows an example of an aircraft with a propeller in a pusher configuration. The term "pusher" refers to the fact that the propulsion unit 360 is mounted at the back of the aircraft and "pushes" the vehicle forward, in contrast to the propulsion unit being mounted at the front of the aircraft. Similar to the description provided for FIG. 2, FIG. 3 depicts common structures used in the pusher plane: a fuselage 320, two horizontal wings 310, vertical stabilizers 330, and a propulsion unit 360, which can include a motor, shaft, and propeller.

UAVs can be launched in various ways, using various types of launch systems (which may also be referred to as deployment systems). A very simple way to launch a UAV is a hand launch. To perform a hand launch, a user holds a portion of the aircraft, preferably away from the spinning rotors, and throws the aircraft into the air while contemporaneously throttling the propulsion unit to generate lift.

Rather than using a hand launch procedure in which the person launching the vehicle is exposed to risk from the quickly spinning propellers, a stationary or mobile launch station can be utilized. For instance, a launch system can include supports, angled and inclined rails, and a backstop. The aircraft begins the launch system stationary on the angled and inclined rails and launches by sufficiently increasing the speed of the propeller to generate forward airspeed along the incline of the launch system. By the end of the angled and inclined rails, the aircraft can have sufficient airspeed to generate lift. As another example, a launch system may include a rail gun or cannon, either of which may launch a UAV by thrusting the UAV into flight. A launch system of this type may launch a UAV quickly and/or may launch a UAV far towards the UAV's destination. Other types of launch systems may also be utilized.

In some cases, there may be no separate launch system for a UAV, as a UAV may be configured to launch itself. For example, a "tail sitter" UAV typically has fixed wings to provide lift and allow the UAV to glide, but also is configured to take off and land vertically on its own. Other examples of self-launching UAVs are also possible.

In a further aspect, various other types of unmanned vehicles may be utilized to provide remote medical support. Such vehicles may include, for example, unmanned ground vehicles (UGVs), unmanned space vehicles (USVs), and/or unmanned underwater vehicles (UUVs). A UGV may be a vehicle which is capable of sensing its own environment and navigating surface-based terrain without input from a driver. Examples of UGVs include watercraft, cars, trucks, buggies, motorcycles, treaded vehicles, and retrieval duck decoys, among others. A UUV is a vehicle that is capable of sensing its own environment and navigating underwater on its own, such as a submersible vehicle. Other types of unmanned vehicles are possible as well.

III. Illustrative Medical-Support Systems with UAVs

As noted above, UAVs may be deployed to provide remote medical support. FIG. 4 is a simplified block diagram illustrating a medical support system 400, according to an example embodiment.

In an illustrative medical-support system 400, an access system 402 may allow for interaction with, control of, and/or utilization of a network of medical-support UAVs 404. In some embodiments, an access system 402 may be a computing system that allows for human-controlled dispatch of UAVs 404. As such, the control system may include or otherwise provide a user interface (UI) 403 via which a user can access and/or control UAVs 404.

As a specific example, access system 402 could be a computing system at a police station or a fire station. Accordingly, a human operator at the police or fire station may receive an indication that a situation exists from a remote device 406 (e.g., a phone call, text message, etc.). The operator may then determine that medical support is appropriate and utilize access system 402 to dispatch one or more UAVs to provide the appropriate medical support. For example, the operator may use the UI 403 of access system 402 to request that a UAV be dispatched to the location of remote device 406 (or to another location indicated by the user of the remote device 406).

A UI 403 of an access system 402 may provide other functionality in addition to allowing for dispatch of UAVs 404. For example, UI 403 may allow an operator to specify certain details related to the medical situation to which the UAV is being dispatched. Examples of such details may include, but are not limited to: (a) general information related to the person or persons involved in the situation, such as age, height, weight, and so on, (b) medical information related to the person or persons involved in the situation, such as medical history, known allergies, and so on, (c) information related to the medical situation itself, such as symptoms exhibited by a person, details of events surrounding the situation (e.g., a car accident), and so on, and (d) desired specifications for the UAV to be dispatched, such as medical-support capabilities, wireless-communication capabilities, and so on.

Further, an access system 402 may provide for remote operation of a UAV. For instance, an access system 402 may allow an operator to control the flight of a UAV via UI 403. As a specific example, an operator may use an access system to dispatch a UAV 404 to the scene of a medical situation. The UAV 404 may then autonomously navigate to the general area where the medical situation is believed to exist (e.g., a stadium). At this point, the operator may use the access system 402 to take over control of the UAV 404, and navigate the UAV to the particular person in need of medical support (e.g., to the person's seat within the stadium). Other examples are also possible.

In an illustrative embodiment, UAVs 404 may take various forms. For example, each UAV 404 may be a UAV such as those illustrated in FIGS. 1 to 3. However, medical support system 400 may also utilize other types of UAVs without departing from the scope of the invention. In some implementations, all UAVs 404 may be of the same or a similar configuration. However, in other implementations, UAVs 404 may include a number of different types of UAVs. For instance, UAVs 404 may include a number of types of UAVs, with each type of UAV being configured for a different type or types of medical support.

A remote device 406 may take various forms. Generally, a remote device 406 may be any device via which a request for medical support can be made and/or via which a situation that may require or benefit from medical support can be reported. For instance, a remote device 406 may be a mobile phone, tablet computer, laptop computer, personal computer, or any network-connected computing device. Further, in some instances, remote device 406 may not be a computing device. As an example, a standard telephone, which allows for communication via plain old telephone service (POTS), may serve as a remote device 406.

Further, a remote device 406 may be configured to communicate with access system 402 via one or more types of communication network(s) 414. For example, a remote device 406 could communicate with access system 402 (or via a human operator of the access system) by placing a phone call over a POTS network, a cellular network, and/or a data network such as the Internet. Other types of networks may also be utilized.

As noted above, a remote device 406 may be configured to allow a user to request medical support. For example, a person may use their mobile phone, a POTS phone, or a VoIP phone, to place an emergency call (e.g., a 9-1-1 call) and request that medical support be provided at the scene of an accident. Further, note that a request for medical support need not be explicit. For instance, a person may place a 9-1-1 call to report an emergency situation. When the 9-1-1 operator receives such a call, the operator may evaluate the information that is provided and decide that medical support is appropriate. Accordingly, the operator may use an access system 402 to dispatch a UAV 404.

In a further aspect, a remote device 406 may be configured to determine and/or provide an indication of its own location. For example, remote device 406 may include a GPS system so that it can include GPS location information (e.g., GPS coordinates) in a communication to an access system 402 and/or to a dispatch system such as central dispatch system 408. As another example, a remote device 406 may use a technique that involves triangulation (e.g., between base stations in a cellular network) to determine its location. Alternatively, another system such as a cellular network may use a technique that involves triangulation to determine the location of a remote device 406, and then send a location message to the remote device 406 to inform the remote device of its location. Other location-determination techniques are also possible.

In an illustrative arrangement, central dispatch system 408 may be a server or group of servers, which is configured to receive dispatch messages requests and/or dispatch instructions from an access system 402. Such dispatch messages may request or instruct the central dispatch system 408 to coordinate the deployment of UAVs for remote medical support. A central dispatch system 408 may be further configured to route such requests or instructions to local dispatch systems 410. To provide such functionality, central dispatch system 408 may communicate with access system 402 via a data network, such as the Internet or a private network that is established for communications between access systems and automated dispatch systems.

In the illustrated configuration, central dispatch system 408 may be configured to coordinate the dispatch of UAVs 404 from a number of different local dispatch systems 410. As such, central dispatch system 408 may keep track of which UAVs 404 are located at which local dispatch systems 410, which UAVs 404 are currently available for deployment, and/or which medical situation or situations each of the UAVs 404 is configured for. Additionally or alternatively, each local dispatch system 410 may be configured to track which of its associated UAVs 404 are currently available for deployment and/or which medical situation or situations each of its associated UAVs is configured for.

In some embodiments, when central dispatch system 408 receives a request for medical support from an access system 402, central dispatch system 408 may select a specific UAV 404 to dispatch. The central dispatch system 408 may accordingly instruct the local dispatch system 410 that is associated with the selected UAV to dispatch the selected UAV. The local dispatch system 410 may then operate its associated deployment system 412 to launch the selected UAV.

As a specific example, central dispatch system 408 may receive a request for medical support that indicates a certain type of medical situation and a location where the situation is occurring. Take, for instance, a request for medical support at the home of a person who appears to have suffered from cardiac arrest. In this scenario, the central dispatch system 408 may evaluate the fleet of UAVs 404 to select the closest available UAV to the person's home that is configured to provide medical support when a heart attack has occurred. Alternatively, the central dispatch system 408 may select an available UAV that is within a certain distance from the person's home (which may or may not be the closest), and which is configured to provide medical support when cardiac arrest has occurred.

In other embodiments, a central dispatch system 408 may forward a request for medical support to a local dispatch system 410 that is near the location where the support is requested, and leave the selection of a particular UAV 404 to the local dispatch system 410. For instance, in a variation on the above example, central dispatch system 408 may forward a request for medical support at the home of a person who appears to have suffered from a heart attack to the local dispatch system 410 that is closest to, or within a certain distance from, the person's home. Upon receipt of the request, the local dispatch system 410 may then determine which of its associated UAVs is configured to provide medical support to a heart-attack victim, and deploy this UAV.

In an example configuration, a local dispatch system 410 may be implemented in a computing system at the same location as the deployment system or systems 412 that it controls. For example, in some embodiments, a local dispatch system 410 could be implemented by a computing system at a building, such as a fire station, where the deployment systems 412 and UAVs 404 that are associated with the particular local dispatch system 410 are also located. In other embodiments, a local dispatch system 410 could be implemented at a location that is remote to its associated deployment systems 412 and UAVs 404.

Numerous variations on and alternatives to the illustrated configuration of medical support system 400 are possible. For example, in some embodiments, a user of a remote device 406 could request medical support directly from a central dispatch system 408. To do so, an application may be implemented on a remote device 406 that allows the user to provide information regarding a medical situation, and generate and send a data message to request medical support. Such an application might also allow the user to request a particular type of medical support (e.g., by requesting that a UAV deliver a certain kind of medicine). In such an embodiment, central dispatch system 418 may include automated functionality to handle requests that are generated by such an application, evaluate such requests, and, if appropriate, coordinate with an appropriate local dispatch system 410 to deploy a UAV.

Further, in some implementations, some or all of the functionality that is attributed herein to central dispatch system 408, local dispatch system(s) 410, access system 402, and/or deployment system(s) 412 could be combined in a single system, implemented in a more complex system, and/or redistributed among central dispatch system 408, local dispatch system(s) 410, access system 402, and/or deployment system(s) 412 in various ways.

Yet further, while each local dispatch system 410 is shown as having two associated deployment systems, a given local dispatch system 410 may have more or less associated deployment systems. Similarly, while central dispatch system 408 is shown as being in communication with two local dispatch systems 410, a central dispatch system may be in communication with more or less local dispatch systems 410.

In a further aspect, a deployment system 412 may take various forms. In general, a deployment system may take the form of or include a system for physically launching a UAV 404. Further, a deployment system 412 may be configured to launch one particular UAV 404, or to launch multiple UAVs 404. A deployment system 412 may further be configured to provide additional functions, including for example, diagnostic-related functions such as verifying system functionality of the UAV, verifying functionality of devices that are housed within a UAV (e.g., such as a defibrillator, a mobile phone or an HMD), and/or maintaining devices or other items that are housed in the UAV (e.g., by charging a defibrillator, mobile phone, or HMD, or by checking that medicine has not expired).

In some embodiments, the deployment systems 412 and their corresponding UAVs 404 (and possibly associated local dispatch systems 410) may be strategically distributed throughout an area such as a city. For example, deployment systems 412 may be located on the roofs of certain municipal buildings, such as fire stations, which can thus serve as the dispatch locations for UAVs 404. Fire stations may function well for UAV dispatch, as fire stations tend to be distributed well with respect to population density, their roofs tend to be flat, and the use of firehouse roofs as leased spaces for UAV dispatch could further the public good. However, deployment systems 412 (and possibly the local dispatch systems 410) may be distributed in other ways, depending upon the particular implementation.

In a further aspect, a medical-support system 400 may include or have access to a user-account database 414. The user-account database 414 may include data for a number of user-accounts, which are each associated with one or more person. For a given user-account, the user-account database 414 may include data related to the associated person or persons' medical history and/or may include other data related to the associated person or persons. Note that the medical-support system may only acquire, store, and utilize data related to a person with that person's explicit permission to do so.

Further, in some embodiments, a person may have to register for a user-account with the medical-support system 400 in order to use or be provided with medical support by the UAVs 404 of medical-support system 400. As such, the user-account database 414 may include authorization information for a given user-account (e.g., a user-name and password), and/or other information that may be used to authorize access to a user-account.

In some embodiments, a person may associate one or more of their devices with their user-account, such that they can be provided with access to the services of medical-support system 400. For example, when a person uses an associated mobile phone to, e.g., place a call to an operator of access system 402 or send a message requesting medical support to a dispatch system, the phone may be identified via a unique device identification number, and the call or message may then be attributed to the associated user-account. In addition or in the alternative to being an authorization mechanism, identifying the user-account may allow information such as the person's medical history to be used in responding to their request for medical support.

In a further aspect, the user-account database 414 may include data indicating a service level for each user. More specifically, a medical-support system 400 may provide service according to a number of different service levels, which correspond to different types of medical support. For example, a higher service level may: (a) provide access to additional types of UAVs, (b) provide medical support for additional medical situations, (c) provide access to improved support for a given medical situation, and/or (d) have priority as far as response time to requests for medical support, as compared to a lower service level. Other differences between a higher and lower service level are also possible.

In some embodiments, there may be no individual user accounts associated with a medical system; or, user accounts may exist but may not be used for purposes of determining whether a person should be provided medical support and/or for purposes of determining the quality of medical support that should be provided. For example, a medical support system may be implemented by a municipality or another public entity to provide medical support to citizens for free or at an equal cost. Other examples are also possible.

IV. Illustrative Components of a Medical-Support UAV

Figure 5:
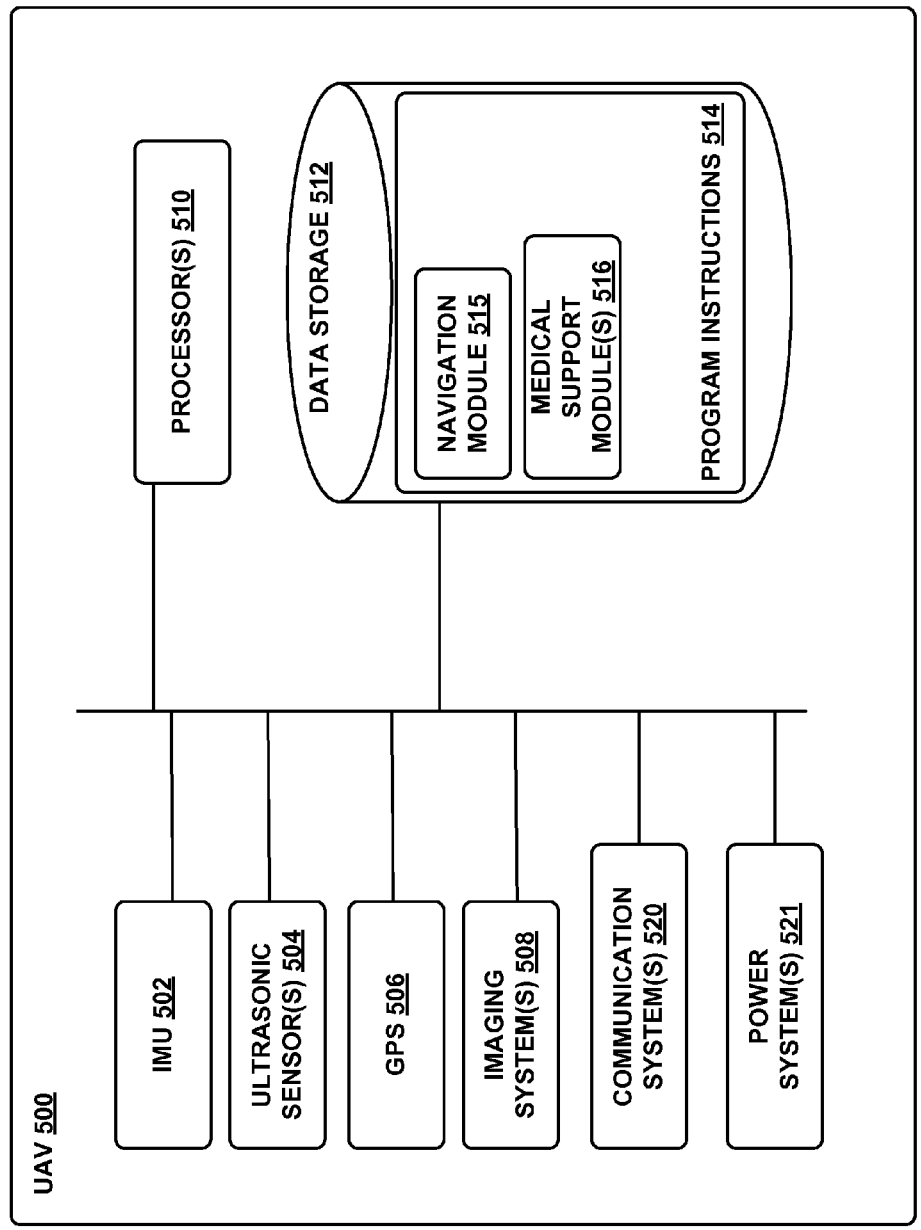
FIG. 5 is a simplified block diagram illustrating components of an unmanned aerial vehicle, according to an example embodiment.

FIG. 5 is a simplified block diagram illustrating components of a UAV 500, according to an example embodiment. UAV 500 may take the form of or be similar in form to one of the UAVs 100, 200, and 300 shown in FIGS. 1 to 3. However, a UAV 500 may also take other forms.

UAV 500 may include various types of sensors, and may include a computing system configured to provide the functionality described herein. In the illustrated embodiment, the sensors of UAV 500 include an inertial measurement unit (IMU) 502, ultrasonic sensor(s) 504, GPS 506, imaging system(s) 508, among other possible sensors and sensing systems.

In the illustrated embodiment, UAV 500 also includes one or more processors 510. A processor 510 may be a general-purpose processor or a special purpose processor (e.g., digital signal processors, application specific integrated circuits, etc.). The one or more processors 510 can be configured to execute computer-readable program instructions 514 that are stored in the data storage 512 and are executable to provide the functionality of a UAV described herein.

The data storage 512 may include or take the form of one or more computer-readable storage media that can be read or accessed by at least one processor 510. The one or more computer-readable storage media can include volatile and/or non-volatile storage components, such as optical, magnetic, organic or other memory or disc storage, which can be integrated in whole or in part with at least one of the one or more processors 510. In some embodiments, the data storage 304 can be implemented using a single physical device (e.g., one optical, magnetic, organic or other memory or disc storage unit), while in other embodiments, the data storage 512 can be implemented using two or more physical devices.

As noted, the data storage 512 can include computer-readable program instructions 514 and perhaps additional data, such as diagnostic data of the UAV 500. As such, the data storage 514 may include program instructions to perform or facilitate some or all of the UAV functionality described herein. For instance, in the illustrated embodiment, program instructions 514 include a navigation module 515 and one or more medical-support modules 516.

A. Sensors

In an illustrative embodiment, IMU 502 may include both an accelerometer and a gyroscope, which may be used together to determine the orientation of the UAV 500. In particular, the accelerometer can measure the orientation of the vehicle with respect to earth, while the gyroscope measures the rate of rotation around an axis. IMUs are commercially available in low-cost, low-power packages. For instance, an IMU 502 may take the form of or include a miniaturized MicroElectroMechanical System (MEMS) or a NanoElectroMechanical System (NEMS). Other types of IMUs may also be utilized.

An IMU 502 may include other sensors, in addition to accelerometers and gyroscopes, which may help to better determine position and/or help to increase autonomy of the UAV 500. Two examples of such sensors are magnetometers and pressure sensors. Other examples are also possible. (Note that a UAV could also include such additional sensors as separate components from an IMU.)

While an accelerometer and gyroscope may be effective at determining the orientation of the UAV 500, slight errors in measurement may compound over time and result in a more significant error. However, an example UAV 500 may be able mitigate or reduce such errors by using a magnetometer to measure direction. One example of a magnetometer is a low-power, digital 3-axis magnetometer, which can be used to realize an orientation independent electronic compass for accurate heading information. However, other types of magnetometers may be utilized as well.

UAV 500 may also include a pressure sensor or barometer, which can be used to determine the altitude of the UAV 500. Alternatively, other sensors, such as sonic altimeters or radar altimeters, can be used to provide an indication of altitude, which may help to improve the accuracy of and/or prevent drift of an IMU.

In a further aspect, UAV 500 may include one or more sensors that allow the UAV to sense objects in the environment. For instance, in the illustrated embodiment, UAV 500 includes ultrasonic sensor(s) 504. Ultrasonic sensor(s) 504 can determine the distance to an object by generating sound waves and determining the time interval between transmission of the wave and receiving the corresponding echo off an object. A typical application of an ultrasonic sensor for unmanned vehicles or IMUs is low-level altitude control and obstacle avoidance. An ultrasonic sensor can also be used for vehicles that need to hover at a certain height or need to be capable of detecting obstacles. Other systems can be used to determine, sense the presence of, and/or determine the distance to nearby objects, such as a light detection and ranging (LIDAR) system, laser detection and ranging (LADAR) system, and/or an infrared or forward-looking infrared (FLIR) system, among other possibilities.

UAV 500 also includes a GPS receiver 506. The GPS receiver 506 may be configured to provide data that is typical of well-known GPS systems, such as the GPS coordinates of the UAV 500. Such GPS data may be utilized by the UAV 500 for various functions. For example, when a caller uses a mobile device to request medical support from a UAV, the mobile device may provide its GPS coordinates. As such, the UAV may use its GPS receiver 506 to help navigate to the caller's location, as indicated, at least in part, by the GPS coordinates provided by their mobile device. Other examples are also possible.

UAV 500 may also include one or more imaging system(s) 508. For example, one or more still and/or video cameras may be utilized by a UAV 500 to capture image data from the UAV's environment. As a specific example, charge-coupled device (CCD) cameras or complementary metal-oxide-semiconductor (CMOS) cameras can be used with unmanned vehicles. Such imaging sensor(s) 508 have numerous possible applications, such as obstacle avoidance, localization techniques, ground tracking for more accurate navigation (e,g., by applying optical flow techniques to images), video feedback, and/or image recognition and processing, among other possibilities.

In a further aspect, UAV 500 may use its one or more imaging system 508 to help in determining location. For example, UAV 500 may capture imagery of its environment and compare it to what it expects to see in its environment given current estimated position (e.g., its current GPS coordinates), and refine its estimate of its position based on this comparison.

In a further aspect, UAV 500 may include one or more microphones. Such microphones may be configured to capture sound from the UAVs environment.

B. Navigation and Location Determination

The navigation module 515 may provide functionality that allows the UAV 500 to, e.g., move about in its environment and reach a desired location. To do so, the navigation module 515 may control the altitude and/or direction of flight by controlling the mechanical features of the UAV that affect flight (e.g., rotors 110 of UAV 100).

In order to navigate the UAV 500 to a target location, a navigation module 515 may implement various navigation techniques, such as map-based navigation and localization-based navigation, for instance. With map-based navigation, the UAV 500 may be provided with a map of its environment, which may then be used to navigate to a particular location on the map. With localization-based navigation, the UAV 500 may be capable of navigating in an unknown environment using localization. Localization-based navigation may involve a UAV 500 building its own map of its environment and calculating its position within the map and/or the position of objects in the environment. For example, as a UAV 500 moves throughout its environment, the UAV 500 may continuously use localization to update its map of the environment. This continuous mapping process may be referred to as simultaneous localization and mapping (SLAM). Other navigation techniques may also be utilized.

In some embodiments, the navigation module 515 may navigate using a technique that relies on waypoints. In particular, waypoints are sets of coordinates that identify points in physical space. For instance, an air-navigation waypoint may be defined by a certain latitude, longitude, and altitude. Accordingly, navigation module 515 may cause UAV 500 to move from waypoint to waypoint, in order to ultimately travel to a final destination (e.g., a final waypoint in a sequence of waypoints).

In a further aspect, navigation module 515 and/or other components and systems of UAV 500 may be configured for "localization" to more precisely navigate to the scene of a medical situation. More specifically, it may be desirable in certain situations for a UAV to be close to the person in need of medical support (e.g., within reach of the person), so as to properly provide medical support to the person. To this end, a UAV may use a two-tiered approach in which it uses a more-general location-determination technique to navigate to a target location or area that is associated with the medical situation, and then use a more-refined location-determination technique to identify and/or navigate to the target location within the general area.

For example, a UAV 500 may navigate to the general area of a person in need using waypoints that are pre-determined based on GPS coordinates provided by a remote device at the scene of the medical situation. The UAV may then switch to mode in which it utilizes a localization process to locate and travel to a specific location of the person in need. For example, if a person is having a heart attack at a large stadium, a UAV 500 carrying a medical package may need to be within reach of the person or someone near the person so that the person can take items from the package. However, a GPS signal may only get a UAV so far, e.g., to the stadium. A more precise location-determination technique may then be used to find the specific location of the person within the stadium.

Various types of location-determination techniques may be used to accomplish localization of a person once a UAV 500 has navigated to the general area of the person. For instance, a UAV 500 may be equipped with one or more sensory systems, such as, for example, imaging system(s) 508, a directional microphone array (not shown), ultrasonic sensors 504, infrared sensors (not shown), and/or other sensors, which may provide input that the navigation module 515 utilizes to navigate autonomously or semi-autonomously to the specific location of a person.

As another example, once the UAV 500 reaches the general area of the person, the UAV 500 may switch to a "fly-by-wire" mode where it is controlled, at least in part, by a remote operator, who can navigate the UAV 500 to the specific location of the person in need. To this end, sensory data from the UAV 500 may be sent to the remote operator to assist them in navigating the UAV to the specific location. For example, the UAV 500 may stream a video feed or a sequence of still images from the UAV's imaging system(s) 508. Other examples are possible.

As yet another example, the UAV 500 may include a module that is able to signal to a passer-by for assistance in either reaching the specific location or delivering its medical-support items to the medical situation; for example, by displaying a visual message in a graphic display, playing an audio message or tone through speakers, flashing a light, or performing a combination of such functions. Such visual or audio message might indicate that assistance is needed in delivering the UAV 500 to the person in need, and might provide information to assist the passer-by in delivering the UAV 500 to the person, such a description of the person, the person's name, and/or a description of the person's specific location, among other possibilities. This implementation can be useful in a scenario in which the UAV is unable to use sensory functions or another location-determination technique to determine the specific location of the person.

As an additional example, once a UAV 500 arrives at the general area of a person, the UAV may utilize a beacon from the remote device (e.g., the mobile phone of a person who called for medical support) to locate the person. Such a beacon may take various forms. As an example, consider the scenario where a remote device, such as the mobile phone of a person in need or a bystander, is able to send out directional signals (e.g., an RF signal, a light signal and/or an audio signal). In this scenario, the UAV may be configured to navigate by "sourcing" such directional signals—in other words, by determining where the signal is strongest and navigating accordingly. As another example, a mobile device can emit a frequency, either in the human range or outside the human range, and the UAV can listen for that frequency and navigate accordingly. As a related example, if the UAV is listening for spoken commands, then the UAV could utilize spoken statements, such as "Help! I'm over here!" to source the specific location of the person in need of medical assistance.

In an alternative arrangement, a navigation module may be implemented at a remote computing device, which communicates wirelessly with the UAV. The remote computing device may receive data indicating the operational state of the UAV, sensor data from the UAV that allows it to assess the environmental conditions being experienced by the UAV, and/or location information for the UAV. Provided with such information, the remote computing device may determine altitudinal and/or directional adjustments that should be made by the UAV and/or may determine how the UAV should adjust its mechanical features (e.g., rotors 110 of UAV 100) in order to effectuate such movements. The remote computing system may then communicate such adjustments to the UAV so it can move in the determined manner.

C. Communication Systems

In a further aspect, UAV 500 includes one or more communication systems 520. The communications systems 520 may include one or more wireless interfaces and/or one or more wireline interfaces, which allow UAV 500 to communicate via one or more networks. Such wireless interfaces may provide for communication under one or more wireless communication protocols, such as Bluetooth, WiFi (e.g., an IEEE 802.11 protocol), Long-Term Evolution (LTE), WiMAX (e.g., an IEEE 802.16 standard), a radio-frequency ID (RFID) protocol, near-field communication (NFC), and/or other wireless communication protocols. Such wireline interfaces may include an Ethernet interface, a Universal Serial Bus (USB) interface, or similar interface to communicate via a wire, a twisted pair of wires, a coaxial cable, an optical link, a fiber-optic link, or other physical connection to a wireline network.

In an example embodiment, a UAV 500 may include communication systems 520 that allow for both short-range communication and long-range communication. For example, the UAV 500 may be configured for short-range communications using Bluetooth and for long-range communications under a CDMA protocol. In such an embodiment, the UAV 500 may be configured to function as a "hot spot;" or in other words, as a gateway or proxy between a remote support device and one or more data networks, such as cellular network and/or the Internet. Configured as such, the UAV 500 may facilitate data communications that the remote support device would otherwise be unable to perform by itself.

For example, UAV 500 may provide a WiFi connection to a remote device, and serve as a proxy or gateway to a cellular service provider's data network, which the UAV might connect to under an LTE or a 3G protocol, for instance. The UAV 500 could also serve as a proxy or gateway to a high-altitude balloon network, a satellite network, or a combination of these networks, among others, which a remote device might not be able to otherwise access.

D. Power Systems

In a further aspect, UAV 500 may include power system(s) 521. A power system 521 may include one or more batteries for providing power to the UAV 500. In one example, the one or more batteries may be rechargeable and each battery may be recharged via a wired connection between the battery and a power supply and/or via a wireless charging system, such as an inductive charging system that applies a time-varying magnetic field to the battery.

E. Medical-Support Functionality

As noted above, UAV 500 may include one or more medical-support modules 516. The one or more medical-support modules 516 include software, firmware, and/or hardware that may help to provide or assist in the provision of the medical-support functionality described herein.

Configured as such, a UAV 500 may provide medical support in various ways. For instance, a UAV 500 may have stored information that can be provided to a person or persons at the target location, in order to assist the person or persons in providing medical care. For example, a UAV may include a video or audio file with instructions for providing medical support, which the UAV can play out to a person at the target location. As another example, a UAV may include an interactive program to assist a person at the target location in providing medical support. For instance, a UAV may include an application that analyzes the person's speech to detect questions related to the medical situation and/or that provides a text-based interface via which the person can ask such questions, and then determines and provides answers to such questions.

In some embodiments, a UAV 500 may facilitate communication between a layperson and/or medical personnel at the scene and medical personnel at a remote location. As an example, a medical support module 516 may provide a user interface via which a person at the scene can use a communication system 520 of the UAV to communicate with an emergency medical technician at a remote location. As another example, the UAV 500 can unlock certain capabilities of a remote device, such as a mobile phone, which is near the UAV at the scene of a medical situation. Such capabilities may be inaccessible to a user of the remote device, unless the remote device is within a certain distance from the UAV such that the UAV can unlock the capabilities. For example, a UAV may send the remote device a security key that allows the remote device to establish a secure connection to communicate with medical personnel at a remote location. Other examples are also possible.

Further, in order to provide medical support at a remote location, a UAV 500 may be configured to transport items to the scene of a medical situation. Such items may aid in diagnosing and/or treating a person who needs medical assistance, or may serve other purposes. Such items may include, as examples: (a) medicines, (b) diagnostic devices, such as a pulse oximeter, blood pressure sensor, or EKG sensor, (c) treatment devices, such as an EpiPen, a first aid kit, or various kinds of defibrillators (e.g., an automated external defibrillator), and/or (d) remote support devices, such as a mobile phone or a head-mountable device (HMD), among other possibilities. Note that some items that are electronic may include one or more batteries to provide power to the item. These batteries may be rechargeable and may be recharged using one or more wired or wireless charging systems. In addition or on in the alternative, an item may be integrated with one or more batteries in the power system 521 for power.

A UAV 500 may employ various systems and configurations in order to transport items to the scene of a medical situation. For example, as shown in FIG. 1, a UAV 100 can include a compartment 135, in which an item or items may be transported. As another example, the UAV can include a pick-and-place mechanism, which can pick up and hold the item while the UAV is in flight, and then release the item during or after the UAV's descent. As yet another example, a UAV could include an air-bag drop system, a parachute drop system, and/or a winch system that is operable from high above a medical situation to drop or lower an item or items to the scene of the medical situation. Other examples are also possible.

In some implementations, a given UAV 500 may include a "package" designed for a particular medical situation (or possibly for a particular set of medical situations). A package may include one or more items for medical support in the particular medical situation, and/or one or more medical-support modules 516 that are designed to provide medical support in the particular medical situation. In some cases, a UAV 500 may include a package that is designed for a particular medical situation such as choking, cardiac arrest, shock, asthma, drowning, etc.

In other cases, a UAV 500 may include a package that is designed for a number of different medical situations, which may be associated in some way. For example, a dive-accident package may be designed to provide or assist in provision of care in various medical situations that are often associated with a scuba diving accident, such as drowning and/or decompression sickness. Such a dive-accident package might include a flotation device, an oxygen-therapy system, a system for delivering visual and/or audible medical care instructions (e.g., instructions for performing CPR), and/or a signaling device, among other possibilities. A UAV 500 that is configured with such a dive-accident package may be referred to herein as a "dive-rescue" UAV. Such a dive-rescue UAV may be deployed to a diver on the surface of the water, who has just had an accident while scuba diving, with the hope that the UAV can reach the diver and deliver medical treatment sooner than would otherwise be possible.

For instance, provided with the above dive-accident package, the UAV 500 may drop a flotation device to help the diver stay afloat until the diver can be reached by rescuers. In addition, the UAV may include a signaling device, which can be automatically turned on when the UAV locates the diver. Doing so may help a rescue boat locate a diver more quickly. Further, once the diver has been rescued, the UAV may display visual instructions and/or play back auditory instructions for CPR, which may help to revive a drowning victim. Such instructions may be particularly useful in the case where the diver is rescued by non-medical professionals; if the diver is rescued by a passing fishing boat, for example.

Further, when the UAV arrives at the scene of a dive accident or, more likely, once the diver has been moved to a rescue boat, the UAV could provide an oxygen-therapy system, and possibly instructions for use thereof, in order to treat possible decompression sickness. Since a rescue boat might not have oxygen-therapy system, and immediate administration of pure oxygen has been shown to increase the probability of recovering from decompression sickness, such functionality of a UAV could improve treatment for a diver suffering from decompression sickness.

In some embodiments, a UAV 500 could include an integrated system or device for administering or assisting in the administration of medical care (e.g., a system or device having one or more components that are built in to the structure of the UAV itself). For example, as noted above, a UAV could include an oxygen-therapy system. In an example configuration, an oxygen-therapy system might include a mask that is connected via tubing to an on-board oxygen source. Configured as such, the UAV could release the oxygen mask when it reaches a person in need of oxygen (e.g., at a fire scene).

As another example of a UAV with an integrated medical-support device, a UAV 500 might function as a mobile defibrillator. Specifically, rather than carry a stand-alone defibrillator that can then be removed from the UAV for use, the UAV itself may function as a defibrillator.

As a specific example, a multicopter might include components of an automated external defibrillator (AED) built into its body, as well as retractable electrode pads for administering a shock to a person who is experiencing a cardiac event or arrest. When the multicopter arrives at the scene of cardiac arrest, the multicopter may land, disable its rotors, and enter a mode where it functions as an AED. Specifically, after landing, the multicopter may release its retractable electrode pads and provide instructions so that a bystander, who might be layperson, could use the electrode pads to administer care to the person with a cardiac arrest. Such instructions may be provided, for example, by displaying text and/or video on a graphic display that is built in to the body of the multicopter, and/or by playing back audio instructions. The multicopter could also include a wireless communication interface via which a bystander could communicate with a live remote operator (e.g., a medical professional at a remote location), in order to receive instructions for using the AED.

Many other examples and variations on the above examples of UAVs with integrated medical-support systems and devices are also possible. For instance, a medical device may be integrated into the structure of a UAV itself when doing so reduces weight, improves aerodynamics, and/or simplifies the use of the device by a person at the scene of the medical situation. Further, those skilled in the art will appreciate that a medical-support system or device may be integrated in the structure of a UAV in other situations and for other reasons.

In some applications, a UAV 500 may be dispatched to the scene of a medical situation to provide early intelligence to medical personnel. In particular, a UAV 500 may be dispatched because it is expected to reach the location of a medical situation more rapidly than medical personnel are able to. In this scenario, the UAV 500 may arrive at the scene and provide early intelligence by communicating information and providing situational awareness to medical personnel. For example, a UAV 500 may use its imaging system(s) 508 to capture video and/or still images at the scene of the medical situation, which the UAV 500 may communicate to medical and/or emergency personnel. As another example, UAV 500 could administer preliminary tests to a person in need, or request that a bystander administer certain preliminary diagnostic tests and/or provide certain information. UAV 500 may then send such test results and/or such information provided by a bystander to medical and/or emergency personnel. A UAV 500 may provide other types of early-intelligence information as well.

By providing early intelligence to medical and/or emergency personnel, a UAV 500 may help the medical and/or emergency personnel to prepare to provide care, such that more effective care can be provided once the personnel arrive at the scene. For instance, a UAV 500 could send video, test results, and/or bystander-provided information to medical personnel while they are travelling in an ambulance on their way to the scene, to firemen or other personnel while they are in a fire truck on their way to the scene, and/or to police they are in a law-enforcement vehicle on their way to the scene, among other possibilities.

It should be understood that the examples of medical-support functionality that are provided herein are not intended to be limited. A UAV may be configured to provide other types of medical-support functionality without departing from the scope of the invention.

V. Illustrative Components of Deployment System

Figure 6:
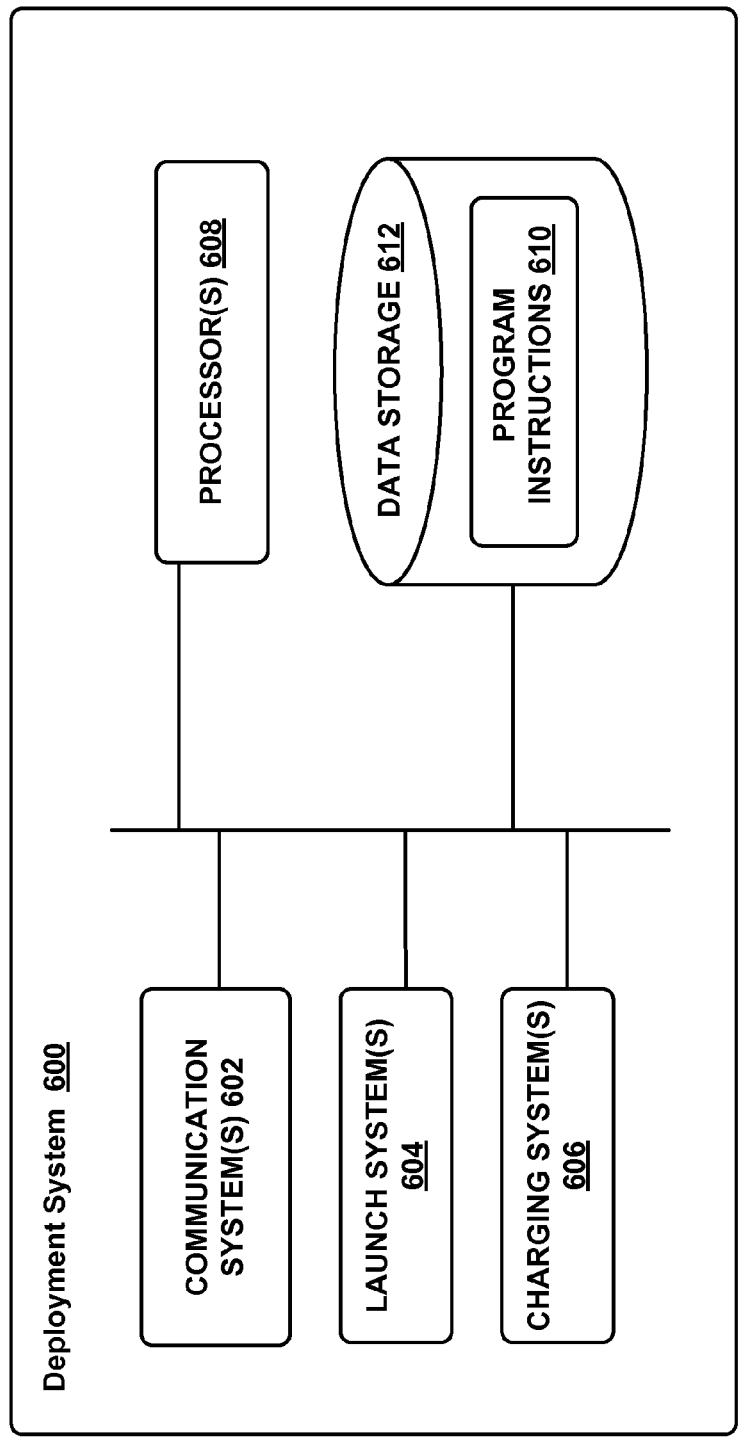
FIG. 6 is a simplified block diagram illustrating components of a deployment system, according to an example embodiment.

FIG. 6 is a simplified block diagram illustrating components of a deployment system 600, according to an example embodiment. As noted above, in addition to launching a UAV 500, a deployment system may perform one or more additional functions, such as diagnostic-related functions. Deployment system 600 may include one or more components to facilitate such functions.

Deployment system 600 may include component such as communication system(s) 602, launch system(s) 604, charging system(s) 606, processor(s) 608, and data storage 612. A communication system 602 may be configured in a same or a similar manner to communication system 520 of the UAV 500. Deployment system 600 may establish a communication link with the UAV 500 via communication systems 602, 520. As such, communication system 602 may be configured to receive data, including for example, diagnostic data corresponding to an object included in the UAV 500 as described in greater detail below.

Launch system 604 may take the form of one or more of the launch systems described above (e.g., one that includes supports, angled and inclined rails, and a backstop, or that includes a rail gun or cannon) and/or any other systems configured to launch one or more UAVs 500. In one example, deployment system 600 may be configured to physically receive UAV 500 such that the UAV 500 may be launched.

Deployment system 600 may be configured to send navigation data to UAV 500 such as via the communication link and before the UAV 500 launches. Navigation data may include any data that UAV 500 may use to navigate itself, including for example, any of the data described above in connection with navigation modules 115. For example, navigation data may include a destination location (or perhaps an identifier that maps to a destination location), one or more waypoint locations and/or other navigation path data that may aid in the UAV 500 reaching is destination. Accordingly, once the UAV 500 is launched, the UAV 500 may use its received navigation data to navigate itself to its destination.

Further, in an example where UAVs are deployed to provide remote medical support, deployment system 600 may also send medical data to the UAV 500, such as via the communication link and before the UAV launches. Medical data may include any data that the UAV 500 or another entity may use to provide medical support, including for example any of the data described above in connection with user-account databases 414 and medical support modules 516. For example, medical data may include medical history for an individual to whom medical attention is intended to be provided.

Charging system 606 may include any type of charging system configured to charge one or more batteries included in UAV 500, including for example, a battery included in power system 521 and/or a battery included in an item (e.g., an AED battery) intended to be transported by UAV 500. In one example, charging system 606 may include a wired charging system, such as where electrical contacts on the battery connect to a power supply. As another example, charging system 606 may include a wireless charging system, such as an inductive charging system where an external time-varying magnetic field is applied to an internal battery. Accordingly, in some instances, deployment system 600 may not need to physically receive a UAV 500, but instead may only need to be proximate to the UAV to perform these or other functions. For example, a UAV 500 could sit atop one roof, while deployment system 600 may be located on a neighboring roof.

Like UAV 500, deployment system 600 may include one or more processors 608 configured to execute computer-readable program instructions 610 that are stored in data storage 612 and that are executable to provide the functionality of a deployment system as described herein. The term "logic module" may be used herein to refer to the combination of a computer-readable medium, a processor, and/or any other components that may cause the deployment system 600 to perform the functions described herein.

Deployment system 600 may also be configured to store one or more items, such as the example medical items described above. As such, a UAV 500 may retrieve an item from the deployment system 600 and transport it to an intended destination.

VI. Illustrative Methods

Figure 7:
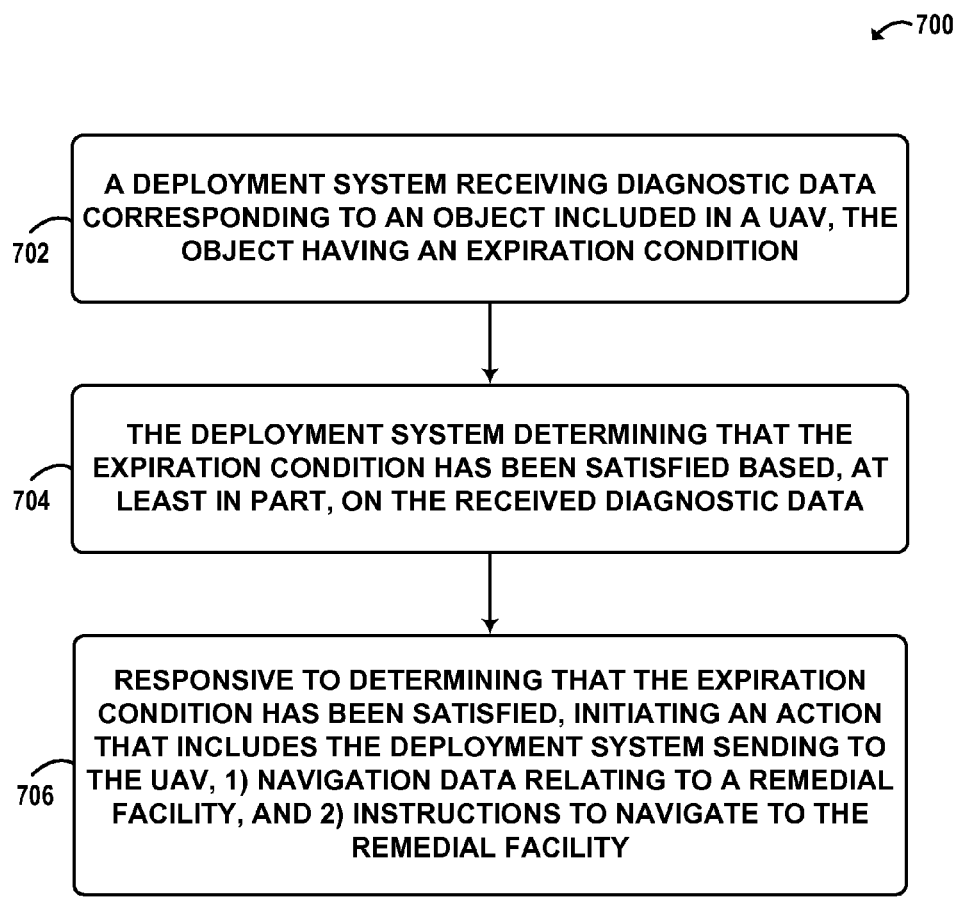
FIG. 7 is a flow chart illustrating a method 700, according to an example embodiment.

FIG. 7 is a flow chart illustrating a method 700, according to an example embodiment. Generally, the method 700 relates to deployment system 600 performing diagnostic-related functions in connection with a UAV 500.

At block 702, the method may involve deployment system 600 receiving diagnostic data corresponding to an object included in a UAV 500, the object having an expiration condition. Such an object may be an item intended for transport by a UAV 500, or a component of the UAV 500 itself (including perhaps a component of an integrated medical system or device) as discussed above. When the expiration condition is satisfied, the object may be considered expired meaning that it needs to be replaced, serviced, or otherwise addressed.

In one example, communication system 602 may establish a communication link with communication system 520, and deployment system 600 may receive the diagnostic data via the communication link. Generally, diagnostic data may include any data of UAV 500 (or the included object) that indicates a historical or current property, condition, setting, or action of UAV 500 (or the included object). For example, diagnostic data may include an expiration time of the object. As another example, diagnostic data may include data from an error log generated by UAV 500 that tracks software, firmware, and/or hardware failures or conditions. As another example, diagnostic data may include data representing a power level of a battery in the UAV 500. As yet another example, diagnostic data may include data from an operational log generated by UAV 500 that tracks actions performed by UAV 500. Other types of diagnostic data are possible. Further, in addition or in the alternative to using the established communication link, deployment system 600 may retrieve diagnostic data from UAV 500 using other techniques, such as by using sensor or imaging systems (not shown).

Diagnostic data may be stored in a data storage, such as in data storage 512. In one example, the diagnostic data may be encoded in an NFC tag associated with (e.g., included in or affixed to) the object, and therefore deployment system 600 may establish a communication link with the NFC tag to retrieve the diagnostic data. In addition or in the alternative, the diagnostic data may be encoded in a bar code or a quick response code associated with the object. However, other techniques for representing the diagnostic data are possible.

At block 704, the method may involve deployment system 600 determining that the expiration condition of the object has been satisfied based, at least in part, on the received diagnostic data. For example, if the received diagnostic data includes an expiration time that has lapsed, deployment system 600 may determine that the expiration condition has been satisfied. However, the diagnostic data may include other data that may allow deployment system 600 to determine that the expiration condition has been satisfied.

At block 706, the method may involve responsive to determining that the expiration condition has been satisfied, initiating an action that includes deployment system 600 sending to UAV 500 navigation data relating to a remedial facility, and further sending to UAV 500 instructions to navigate to the remedial facility based, at least in part, on the navigation data. The deployment system may further instruct the UAV 500 to return back to the deployment system 600 with the replaced or services object. The deployment system 600 may initiate other actions that facilitate remedying the issued in connection with the expired object. Such actions may be determined based on a table or other data structure (e.g., stored in data storage 612) that map an expiration condition to an action.

The initiated action may further include deployment system 600 launching UAV 500 (e.g., via the launch systems 604) to assist UAV 500 in navigating to the remedial facility. In one example, a remedial facility may be an item-replacement facility that is configured to replace expired objects with replacement non-expired objects. In another example, a remedial facility may be a maintenance facility that is configured to service, or otherwise address an expired object such that it may be may no longer be considered expired. A remedial facility may be remotely located and may serve as a "central" remedial facility such that it may provide such services for multiple UAVs 500 (e.g., within a particular geographical area), however, other configurations are also possible.

Several example applications of the method 700 will now be provided. In one example application, the object may be a particular type of medical item, namely medicine, intended for transport by the UAV 500. Medicine often has an expiration time, and therefore an expiration condition of the medicine may be satisfied if the expiration time lapses. Notably, as used herein, the term "time" refers to a time of day, a date, a time of day and a date, and/or any other temporal indicator. In this example, the deployment system 600 may cause the UAV 500 to navigate to a remedial facility that may be configured to replace the expired medicine with medicine that has not expired.

As another example application, the object may be another type of medical item, namely an oxygen tank. For an oxygen tank, an expiration condition may be satisfied if an amount of oxygen stored therein falls below a threshold amount. In this example, the deployment system 600 may cause the UAV 500 to navigate to a remedial facility that may be configured to refill the oxygen tank with more oxygen.

As another example application, the object may be a component of a system integrated with the UAV 500. For example, the object may be a battery component of an AES integrated in the UAV 500. As such, the expiration condition of the battery may be satisfied if the battery is nearing a state in which the battery is unable to be recharged. This may be determined, for example, based on an indication of the number of recharges applied to the battery and/or a failure of the battery to discharge across an expected range at an expected rate. In this example, the deployment system 600 may cause the UAV 500 to navigate to a remedial facility that may be configured to service or replace the battery.

As another example application, the object may be a component of the UAV 500, such as a wheel, wing, or battery (i.e., to provide power to the UAV 500 itself). For such a component, the expiration condition may be satisfied if the UAV has logged a threshold number of flight hours while using the component. Alternatively, the expiration condition may be satisfied if the component shows certain signs of wear or damage (e.g., due to a flight-related incident or a manufacturing defect). This may be determined for example, based on an operational log or a physical property of the object (e.g., as a result of a chemical reaction). In this example, the deployment system 600 may cause the UAV 500 to navigate to a remedial facility that may be configured to service or replace the component.

In the instance where the object is a battery that powers the UAV 500 and the battery is low on power, the initiated action may further include deployment system 600 recharging the battery (e.g., by using the charging system 606). This technique may ensure that UAV 500 has sufficient battery power to navigate to its intended remedial facility.

As noted, the applications of the method 700 provided above are mere examples. Indeed, a wide variety of different objects and corresponding expiration conditions and actions are contemplated.

Figure 8:
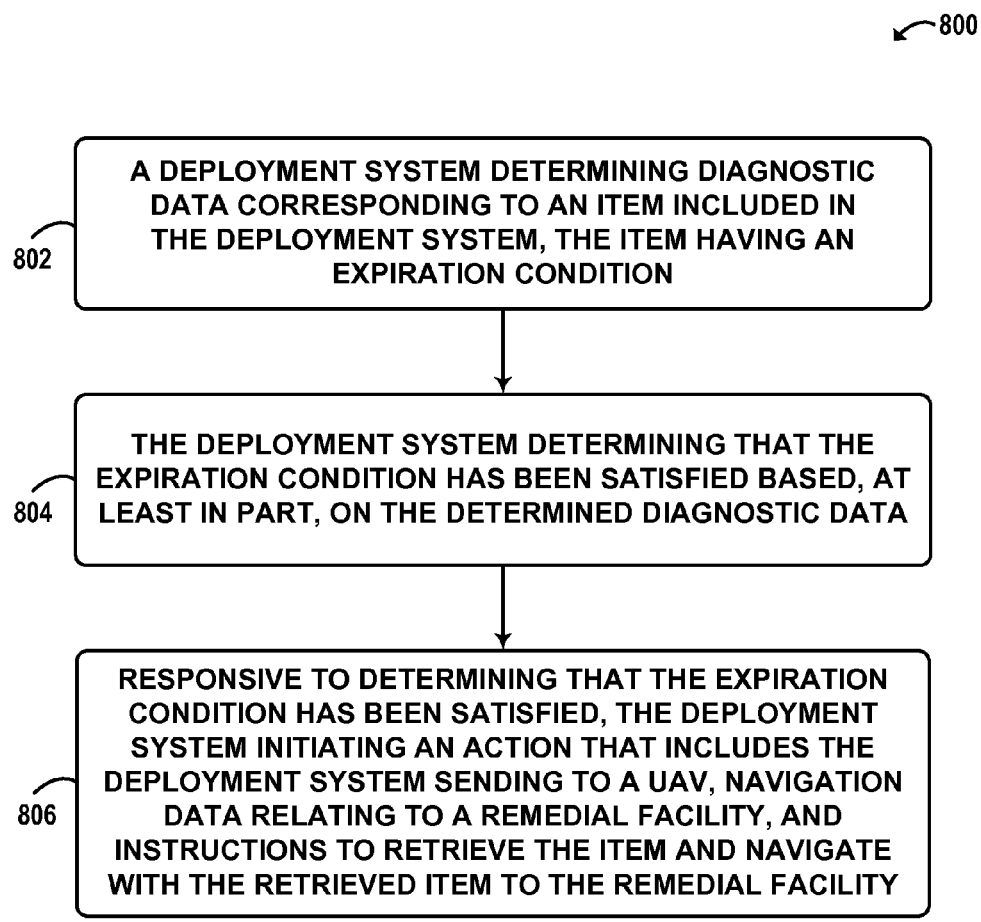
FIG. 8 is a flow chart illustrating a method 800, according to an example embodiment.

FIG. 8 is a flow chart illustrating a method 800, according to an example embodiment. As noted above, a deployment system 600 may store one or more items that may be retrieved and transported by UAV 500. As such, method 800 relates to a deployment system 600 that may perform diagnostic-related functions in connection with an item stored therein.

At block 802, the method may involve the deployment system 600 determining diagnostic data corresponding to an item included in the deployment system (e.g., from an NFC tag on the item as described above). At block 804, the method may involve the deployment system 600 determining that the expiration condition has been satisfied based, at least in part, on the determined diagnostic data.

At block 806, the method may involve responsive to determining that the expiration condition has been satisfied, the deployment system 600 initiating an action that includes sending to a UAV 500 navigation data relating to a remedial facility, and instructions to retrieve the item and navigate with the retrieved item to the remedial facility based, at least in part, on the navigation data.

Figure 9:
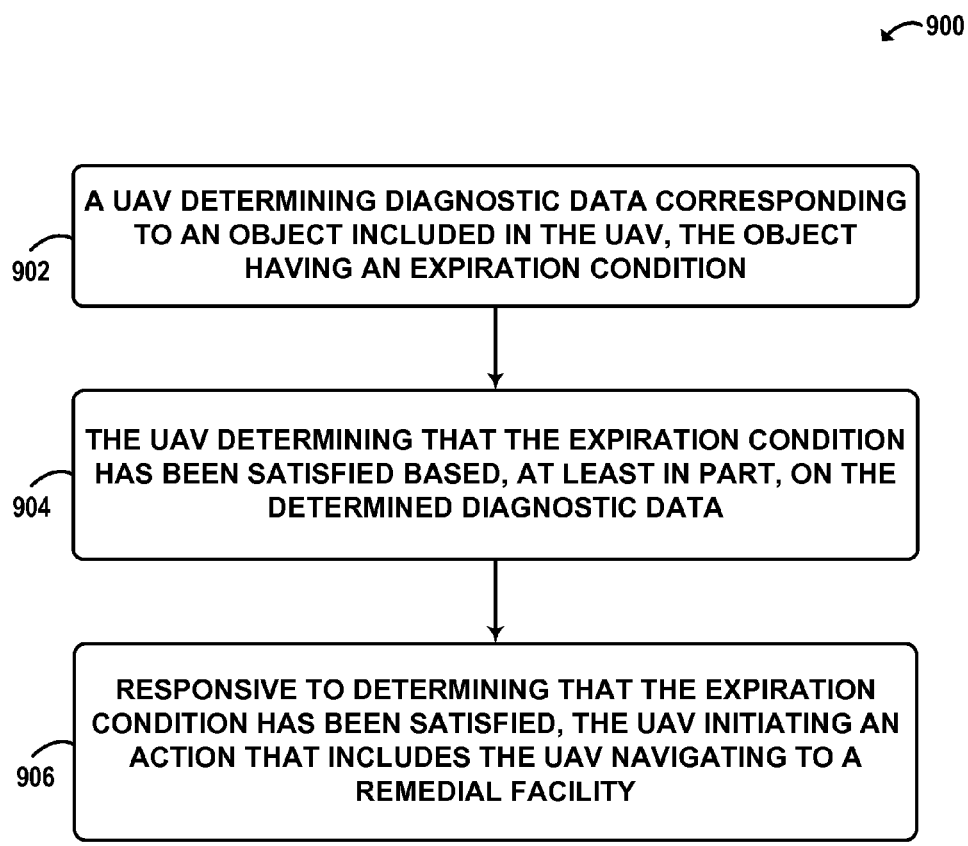
FIG. 9 is a flow chart illustrating a method 900, according to an example embodiment.

FIG. 9 is a flow chart illustrating a method 900, according to an example embodiment. Method 900 is a variation of method 700 and method 800 where the UAV 500 itself performs diagnostic-related functions to address instances in which an object included in the UAV has expired.

At block 902, the method may involve the UAV 500 determining diagnostic data (e.g., from an error or operational log, or from an NFC tag) corresponding to an object included in the UAV, the object having an expiration condition.

At block 904, the method may involve the UAV 500 determining that the expiration condition has been satisfied based, at least in part, on the determined diagnostic data.

At block 906, the method may involve responsive to determining that the expiration condition has been satisfied, the UAV 500 initiating an action that includes the UAV navigating to a remedial facility (e.g., using the navigation module 515).

In one example, the UAV 500 may determine an appropriate remedial facility that the UAV 500 navigates to according to the type of included object and/or the type of expiration condition that was satisfied. For example, one remedial facility may be configured to replace medicine, while another may be configured to service certain components of a UAV 500. In another example, each UAV 500 may have a corresponding remedial facility 500 to which the UAV 500 navigates to as described above. For example, the corresponding remedial facility may be one that is nearest to the UAV 500, or that meets some other defined criteria. Notably, in some instances, a deployment system 600 may also be a remedial facility.

In one example, a remedial facility that corresponds to a UAV 500 may be determined by the central dispatch system 408, such as based on a request received via the user interface 403 of the access system 402. In such an example, the central dispatch system 408 may send a message to a UAV 500 to alert the UAVs 500 of its determined corresponding remedial facility (which may replace a previously determined one). The central dispatch system 408 may also await receipt of a confirmation message sent from the UAVs 500 indicating that the update message was received. In the event that a confirmation message is not received from a particular UAV 500, an alert may be generated indicating that the UAV 500 is in need of a manual inspection. Such an alert may be provided, for example via the user interface 403 of the access system 402.

All features and variations discussed in connection with method 700 are likewise applicable to method 800 and method 900.

VII. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

While one or more of the functions described herein have been described as being performed by the certain entities (e.g., the deployment system 600 or the UAV 500), such functions may be performed by any entity. Further, the functions described throughout this disclosure need not be performed in the disclosed order. Also, not all steps need to be performed to achieve the desired advantages of the disclosed system and method, and therefore not all functions are required.

It is contemplated that alternative data structure and storage techniques may be employed in implementing the functions described herein (e.g., data stored in a table may instead be stored in a linked-list, tree, or other data structure).

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

The invention claimed is:

1. A deployment system comprising:
    a communication system configured for receiving diagnostic data corresponding to an object held by an unmanned aerial vehicle (UAV), wherein the object has an expiration condition; and
    a logic module configured for (i) determining that the expiration condition has been satisfied based, at least in part, on the received diagnostic data, and (ii) responsive to determining that the expiration condition has been satisfied, initiating an action that comprises sending to the UAV both (a) navigation data relating to a remedial facility, and (b) instructions to navigate to the remedial facility based, at least in part, on the navigation data.

2. The deployment system of claim 1, wherein the initiated action further comprises launching the UAV.

3. The deployment system of claim 1, wherein the object comprises a medical item.

4. The deployment system of claim 1, wherein determining that the expiration condition has been satisfied comprises determining that an expiration time of the object has lapsed.

5. The deployment system of claim 1, wherein the object is associated with a near-field communication (NFC) tag, and wherein receiving the diagnostic data comprises detecting and determining the diagnostic data from the NFC tag.

6. A method comprising:
    receiving, by a deployment system, diagnostic data corresponding to an object held by an unmanned aerial vehicle (UAV), wherein the object has an expiration condition;
    determining that the expiration condition has been satisfied based, at least in part, on the received diagnostic data; and
    responsive to determining that the expiration condition has been satisfied, initiating an action that comprises sending to the UAV both (i) navigation data relating to a remedial facility, and (ii) instructions to navigate to the remedial facility based, at least in part, on the navigation data.

7. The method of claim 6, wherein the initiated action further comprises launching the UAV.

8. The method of claim 6, wherein the object comprises a medical item.

9. The method of claim 6, wherein determining that the expiration condition has been satisfied comprises determining that an expiration time of the object has lapsed.

10. The method of claim 6, wherein the object is associated with a near-field communication (NFC) tag, and wherein receiving the diagnostic data comprises detecting and determining the diagnostic data from the NFC tag.

11. A non-transitory computer-readable storage medium having stored thereon program instructions that, when executed by a processor, cause performance of a set of functions, the set including:
    receiving, by a deployment system, diagnostic data corresponding to an object held by an unmanned aerial vehicle (UAV), wherein the object has an expiration condition;
    determining that the expiration condition has been satisfied based, at least in part, on the received diagnostic data; and
    responsive to determining that the expiration condition has been satisfied, initiating an action that comprises sending to the UAV both (i) navigation data relating to a remedial facility, and (ii) instructions to navigate to the remedial facility based, at least in part, on the navigation data.

12. The computer-readable medium of claim 11, wherein the initiated action further comprises launching the UAV.

13. The computer-readable medium of claim 11, wherein the object comprises a medical item.

14. The computer-readable medium of claim 11, wherein determining that the expiration condition has been satisfied comprises determining that an expiration time of the object has lapsed.

15. The computer-readable medium of claim 11, wherein the object is associated with a near-field communication (NFC) tag, and wherein receiving the diagnostic data comprises detecting and determining the diagnostic data from the NFC tag.

16. A deployment system comprising:
a logic module configured for (i) determining diagnostic data corresponding to an item held by an unmanned aerial vehicle (UAV), wherein the item has an expiration condition, (ii) determining that the expiration condition has been satisfied based, at least in part, on the determined diagnostic data, and (ii) responsive to determining that the expiration condition has been satisfied, initiating an action that comprises sending to the UAV (a) navigation data relating to a remedial facility, and (b) instructions to retrieve the item and navigate with the retrieved item to the remedial facility based, at least in part, on the navigation data.

17. The deployment system of claim 16, wherein the initiated action further comprises launching the UAV.

18. The deployment system of claim 16, wherein the item comprises a medical item.

19. The deployment system of claim 16, wherein determining that the expiration condition has been satisfied comprises determining that an expiration time of the item has lapsed.

20. The deployment system of claim 16, wherein the item is associated with a near-field communication (NFC) tag, and wherein determining the diagnostic data comprises detecting and determining the diagnostic data from the NFC tag.

21. An unmanned aerial vehicle (UAV) comprising:
a navigation module; and
a logic module configured for (i) determining diagnostic data corresponding to an object held by the UAV, wherein the object has an expiration condition; (ii) determining that the expiration condition has been satisfied based, at least in part, on the determined diagnostic data; and (iii) responsive to determining that the expiration condition has been satisfied, initiating an action that comprises the UAV using the navigation module to navigate to a remedial facility.

22. The UAV of claim 21, further comprising a communication system, wherein the logic module is further configured to determine the remedial facility based on a message received via the communication system.

23. The UAV of claim 21, wherein the initiated action further comprises the UAV launching itself.

24. The UAV of claim 21, wherein the object comprises a medical item.

25. The UAV of claim 21, wherein determining that the expiration condition has been satisfied comprises determining that an expiration time of the object has lapsed.

* * * * *